(12) United States Patent
Hilpert et al.

(10) Patent No.: US 9,301,497 B2
(45) Date of Patent: Apr. 5, 2016

(54) DEVICE FOR SAMPLING TISSUE FROM AN ANIMAL AND CORRESPONDING STORAGE MEANS

(75) Inventors: Jean-Jacques Hilpert, Vitre (FR); Johan Decaluwe, Laval (FR)

(73) Assignee: Allflex Europe (FR)

( * ) Notice: Subject to any disclaimer, the term of this patent is extended or adjusted under 35 U.S.C. 154(b) by 970 days.

(21) Appl. No.: 13/139,948

(22) PCT Filed: Dec. 18, 2009

(86) PCT No.: PCT/EP2009/067591
§ 371 (c)(1),
(2), (4) Date: Sep. 23, 2011

(87) PCT Pub. No.: WO2010/070130
PCT Pub. Date: Jun. 24, 2010

(65) Prior Publication Data
US 2012/0010526 A1 Jan. 12, 2012

(30) Foreign Application Priority Data
Dec. 19, 2008 (FR) ..................................... 08 07265

(51) Int. Cl.
*A61B 10/00* (2006.01)
*A61B 17/3205* (2006.01)
*A01K 11/00* (2006.01)
*A61B 10/02* (2006.01)

(52) U.S. Cl.
CPC ........... *A01K 11/003* (2013.01); *A61B 10/0096* (2013.01); *A61B 10/0266* (2013.01); *A61B 17/32053* (2013.01)

(58) Field of Classification Search
CPC .............. A01K 11/003; A01K 11/001; A61B 10/0266; A61B 10/0096; A61B 10/02
USPC ........................................ 600/562, 564, 567
See application file for complete search history.

(56) References Cited

U.S. PATENT DOCUMENTS 2,570,048 A 10/1951 Cooke et al.
2,617,359 A * 11/1952 Van Horn et al. .............. 102/512
4,885,855 A * 12/1989 Marks et al. .................... 40/301

(Continued)

FOREIGN PATENT DOCUMENTS

EP 1024354 A1 8/2000
EP 1504722 2/2005

(Continued)

OTHER PUBLICATIONS

Written Opinion for International Application PCT/EP2009/067501, Opinion completed Aug. 2, 2011, 7 pgs.

(Continued)

*Primary Examiner* — Sean Dougherty
(74) *Attorney, Agent, or Firm* — KPPB LLP

(57) ABSTRACT

The invention relates to a device for sampling tissue from an animal, comprising sampling means provided with at least one cutting element (35) for cutting and collecting a sample of tissue from the animal, and means (31) for storing the sample, into which the cutting element is inserted once the sample has been collected. According to the invention, the storage means (31) have at least two openings, a first opening (32) for receiving the cutting element and the sample, and a second opening (33) cooperating with the detachable closing means (34).

18 Claims, 6 Drawing Sheets

(56) References Cited

U.S. PATENT DOCUMENTS

| | | | |
|---|---|---|---|
| 5,005,433 A | 4/1991 | Patton et al. | |
| 5,156,160 A | 10/1992 | Bennett et al. | |
| 5,268,148 A * | 12/1993 | Seymour | 422/419 |
| 5,388,588 A | 2/1995 | Nabai et al. | |
| 5,482,008 A * | 1/1996 | Stafford et al. | 119/174 |
| 5,526,822 A * | 6/1996 | Burbank et al. | 600/567 |
| 6,080,173 A * | 6/2000 | Williamson et al. | 606/184 |
| 6,196,978 B1 | 3/2001 | Weilandt et al. | |
| 6,509,187 B2 * | 1/2003 | Brem | 435/288.2 |
| 6,659,338 B1 * | 12/2003 | Dittmann et al. | 235/375 |
| 6,968,639 B2 * | 11/2005 | Destoumieux | 40/301 |
| 7,198,629 B2 * | 4/2007 | Brem | 606/116 |
| 7,235,055 B2 * | 6/2007 | Pfistershammer | 600/567 |
| 8,517,957 B2 * | 8/2013 | Decaluwe et al. | 600/567 |
| 2004/0167429 A1 | 8/2004 | Roshdieh et al. | |
| 2004/0242960 A1 * | 12/2004 | Orban, III | 600/106 |
| 2005/0228310 A1 * | 10/2005 | Pfistershammer | 600/567 |
| 2005/0256425 A1 | 11/2005 | Prusiner et al. | |
| 2007/0142743 A1 | 6/2007 | Provencher et al. | |
| 2007/0293826 A1 | 12/2007 | Wall et al. | |
| 2008/0044313 A1 * | 2/2008 | Caisley | 422/102 |
| 2008/0064983 A1 | 3/2008 | Stromberg et al. | |
| 2008/0227662 A1 | 9/2008 | Stromberg et al. | |
| 2008/0228105 A1 | 9/2008 | Howell et al. | |
| 2009/0131825 A1 * | 5/2009 | Burbank et al. | 600/567 |
| 2010/0016758 A1 * | 1/2010 | Hilpert | 600/567 |
| 2012/0010526 A1 * | 1/2012 | Hilpert et al. | 600/564 |
| 2013/0204159 A1 | 8/2013 | Destoumieux et al. | |
| 2013/0211287 A1 * | 8/2013 | Decaluwe et al. | 600/562 |
| 2013/0211416 A1 * | 8/2013 | Teychene et al. | 606/117 |

FOREIGN PATENT DOCUMENTS

| | | |
|---|---|---|
| EP | 1759638 A1 | 3/2007 |
| EP | 1772104 | 4/2007 |
| WO | 9626675 A1 | 9/1996 |
| WO | 0189388 A1 | 11/2001 |
| WO | 0239810 A2 | 5/2002 |
| WO | 02078431 A2 | 10/2002 |
| WO | 2005110602 A1 | 11/2005 |
| WO | 2007087355 A2 | 8/2007 |
| WO | 2008003693 A1 | 1/2008 |
| WO | 2008055690 A1 | 5/2008 |
| WO | 2010066475 A1 | 6/2010 |

OTHER PUBLICATIONS

Search Report and Written Opinion for International Application PCT/EP2011/059636, completed Jul. 8, 2011.

Search Report for French Application 1054563, completed Jan. 13, 2011, 2 pages.

* cited by examiner

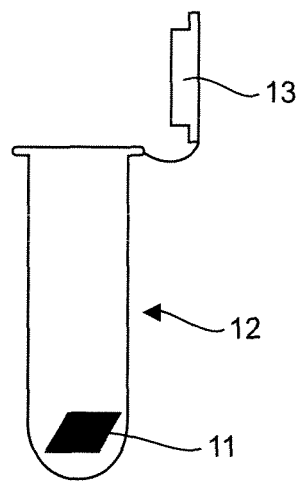
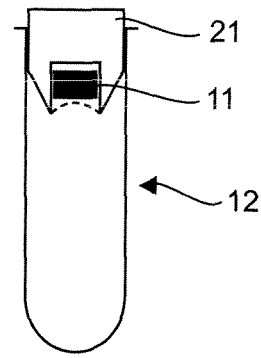
Fig. 1    Fig. 2
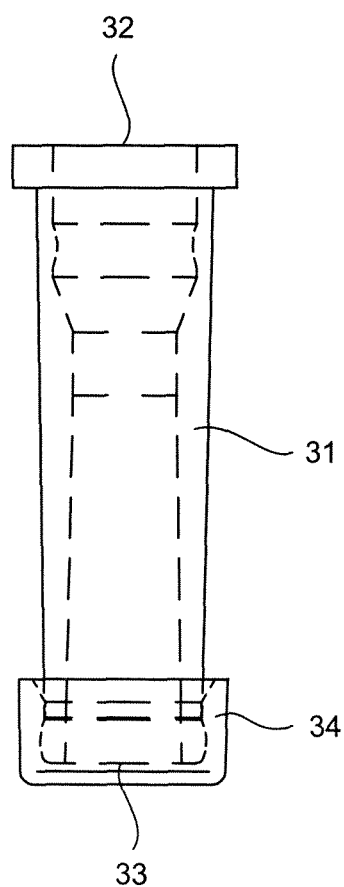
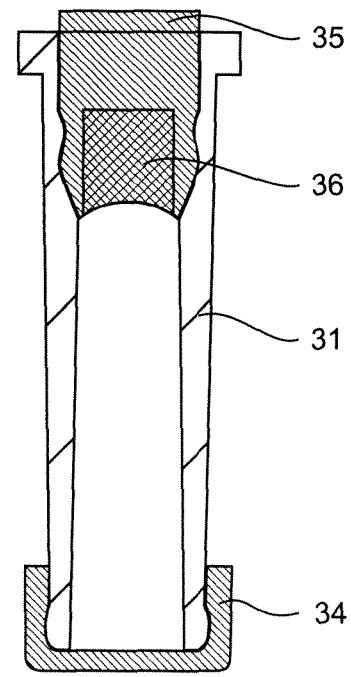
Fig. 3A    Fig. 3B

DEVICE FOR SAMPLING TISSUE FROM AN ANIMAL AND CORRESPONDING STORAGE MEANS

FIELD OF THE INVENTION

The field of the invention is that of the control and/or identification of animals.

More specifically, the invention relates to the sampling of animal tissue, enabling in particular the cells with biological or biochemical characteristics of the animal to be preserved, for example in order to subsequently identify the animal or detect diseases in the animal. Such samplings are, for example, performed when placing a marking device, also called a mark.

The invention enables in particular the sample of tissue on bovines, ovines, porcines, caprines, birds, fish or more generally on any animal species.

PRIOR ART

To improve the monitoring of livestock and guarantee the origin of animals intended in particular for consumption, for example by detecting diseases, tissue samples from the animals concerned are increasingly being collected.

Such a sample can be performed directly on the animal, at birth, for example, or when placing an identification mark on the animal.

Once collected, the tissue sample of the animal can be stored and/or sent to a laboratory for analysis.

To take a sample when placing an identification mark on an animal, a mark including a male portion having a hollow rod and a female portion, intended to at least partially receive the rod, is classically used. The hollow rod enables a punch to pass, which can be removed after the mark has been placed. Such a punch has a cutting edge enabling the animal's skin to be perforated when placing the mark.

Thus, when the male and female portions are fitted together, the punch perforates the animal's skin along a contact line, and guides the rod into the female portion. The tissue sample cut by the cutting edge remains contained in the punch. After the punch is removed, the sample can be extracted from the punch and stored. The sample can also be preserved for some time in the punch.

For example, as shown in FIG. 1, a tissue sample 11 taken from an animal can be stored in a microtube 12 in the form of a cap. Such a microtube 12 can be closed by a lid 13, optionally connected to the microtube 12.

A preservative agent can also be introduced into the microtube 12, making it possible in particular to dry the sample and ensure its preservation over a long time, from several months to several years, for example.

A disadvantage of this technique is that the operations of extracting the sample 11 from the punch and inserting it into the microtube 12 are very delicate. In particular, there is a risk of contamination of the sample during these operations.

Other sampling techniques have also been proposed, making it possible to directly insert the sample into the microtube during sampling. These techniques can be implemented independently of, or in conjunction with the placing of the mark.

As shown in FIG. 2, these techniques are based on the use of a punch or cutter forming or including a cutting element 21, intended to cut a sample 11 of tissue from the animal and to collect it in a housing. The punch or cutter 21, attached to a first jaw of a sampling tool such as a clamp, for example, cuts the animal's skin and is inserted at least partially into the microtube 12, attached to a second jaw of the tool, as the tool is actuated. The punch 21 classically has a diameter slightly smaller than that of the microtube 12, so as to serve as a hermetic lid on the microtube. The housing receiving the sample 11 therefore opens toward the inside of the microtube, but is closed toward the outside of the microtube, so as to prevent contamination of the sample.

Owing to these sampling techniques, the sample 11 is directly inserted into the microtube 12, thus limiting the risk of contamination of the sample.

A disadvantage of this technique is that, once the punch 21 has been inserted into the microtube 12, it is no longer possible to add product to the microtube, such as a preservative agent or a reagent, without having to remove or cut the punch 21.

There is therefore a need for a new technique for sampling tissue of an animal that does not have all of these disadvantages of the prior art.

SUMMARY OF THE INVENTION

The invention proposes a novel solution that does not have all of these disadvantages of the prior art, in the form of an animal tissue sampling device including:
- sampling means having at least one cutting element intended to cut and collect an animal tissue sample, and
- means for storing the sample into which the cutting element is inserted after the sample has been collected.

According to the invention, the storage means have:
- a first opening enabling said cutting element and said sample to be received, in which said cutting element blocks said first opening after insertion therein; and
- a second opening, distinct from said first opening, and cooperating with removable closure means in order to enable said sample to be extracted.

The invention is thus based on a novel and inventive approach to sampling and storage of animal tissue, making it possible to collect a sample without the risk of contaminating it. Indeed, the cutting element and the sample are directly inserted into the storage means, without any external intervention in order to remove the sample from the sampling means, and to insert the sample into the storage means.

In an inventive manner, the storage means according to the invention have at least two openings. In this way, when the cutting element (or a punch including the cutting element) and the sample are inserted into the storage means and at least partially block the first opening, it is still possible to add a product such as a preservative agent or a reagent to the storage means by means of the second opening, without having to remove the sample.

In addition, it is not necessary according to the invention to remove or cut the cutting element (or the punch including the cutting element) blocking the first opening in order to analyze the sample.

According to a specific embodiment, the storage means include at least one wall defining two compartments each associated with one of said openings.

In this way, the first compartment, associated with the first opening, makes it possible to receive the sample. This first opening is at least partially blocked by the cutting element. The second compartment, associated with the second opening, is closed by removable closure means.

The wall thus makes it possible, inter alia, to secure the sample in the first compartment. Indeed, owing to this wall, the sample is not accessible to a cheater, without forcefully removing or cutting the cutting element (or the punch including the cutting element).

Such a wall is advantageously permeable, i.e. it is not impervious.

It enables in particular the passage of liquid, gas or small elements from one compartment to the other. Thus, it enables the passage of a reagent, introduced through the second opening, from the second compartment to the first compartment. However, it prevents the passage of the sample located in the first compartment to the second compartment.

Balls of preservative agent, enabling the sample to dry, can also be introduced into the second compartment.

The permeable wall then makes it possible to prevent the passage of the balls from the second compartment to the first compartment. Indeed, it is preferable for these balls not to be in direct contact with the sample, so as to prevent the sample from being denatured or to prevent problems during analyses (clogged pipettes, for example).

However, the permeability of the wall enables the drying agent to act on the entire volume of the tube, i.e. in the first and second compartments, by drying the ambient air and the sample, which can then be preserved.

Owing to the second opening, it is thus possible to introduce such balls into the storage means, before or after insertion of the sample, and to preserve these balls in the storage means for the entire sample storage period. Once the sample is to be analyzed, it is possible to remove these balls from the storage means, owing to the second opening cooperating with removable closure means. The second opening therefore makes it possible to insert and remove these balls as desired.

In this way, during analysis of the sample, these balls or other liquid, gas or element present in the storage means can be removed, thereby preventing the analysis from being distorted, in particular when said balls, liquid, gas or other element react with a reagent used.

In addition, the removal of the drying agents makes it possible to reduce the amount of reagent injected, as the reagent is no longer absorbed by these drying agents.

For example, the wall includes an element belonging to the group including:
- a membrane;
- a grid; or
- a partition perforated with at least one opening.

According to a specific embodiment, the storage and/or closure means contain at least one drying agent.

A drying agent makes it possible in particular to improve the preservation of the sample, by absorbing the water contained in the sample. It is, for example, Silica Gel (registered trademark) or more generally a molecular sieve. Different types of product based on silica, clay or the like in the form of balls, powder, gel, solid, liquid, and so on can therefore be used.

In particular, a drying agent can be inserted into the removable closure means. Thus, if these closure means are in the form of a cap, balls of drying agent can be provided inside said cap.

According to a specific feature of the invention, the storage means have a revolution shape, with the first and second openings being located at the ends of the revolution shape. For example, the storage means form a tube open at the two ends.

In particular, the closure means are reversibly secured to the storage means, the storage means including first securing means, and the closure means include second securing means complementary to said first securing means.

For example, the closure means include a hermetic seal (i.e., cap, lid, or plug) reversibly secured to the storage means by fitting, dipping or screwing.

According to another embodiment of the invention, the sampling means include a removable protection element arranged in the extension of the cutting element and extending over at least a substantial portion of a rod-forming element of the sampling tool when the sampling means are secured to the tool.

This protection element makes it possible in particular to prevent the contamination of animals by one another when the same tool is used to sample tissue of different animals.

According to another aspect of the invention, the device includes anti-return means, designed so as to enable the passage of a sample and the separation thereof from the sampling means.

These anti-return means can in particular be formed by a washer perforated at its center and having a plurality of flexible strips or claws extending toward said center.

According to another aspect of the invention, the storage means contain a preservative and/or reactive liquid.

In this case, it is possible to provide a sealing lid, isolating said liquid and capable of being perforated when a sample is inserted.

It should be noted that these last two aspects can also be implemented independently of the presence of two openings, in certain approaches.

The invention also relates to means for storing an animal tissue sample in which a cutting element, intended to cut and collect an animal tissue sample, is inserted after collection of said sample.

According to the invention, the storage means have:
- a first opening enabling said cutting element and said sample to be received, in which said cutting element blocks said first opening after it is inserted therein; and
- a second opening, distinct from said first opening, and cooperating with removable closure means so as to enable said sample to be extracted.

LIST OF FIGURES

Other features and advantages of the invention will become clear from the following description of a specific embodiment, provided as a simple illustrative and non-limiting example, and the appended drawings, in which:

FIGS. 1 and 2 show means for storing a tissue sample according to the prior art;

FIGS. 3A and 3B show storage means associated with removable closure means according to an embodiment of the invention;

DESCRIPTION OF A SPECIFIC EMBODIMENT OF THE INVENTION

Figure 4A:
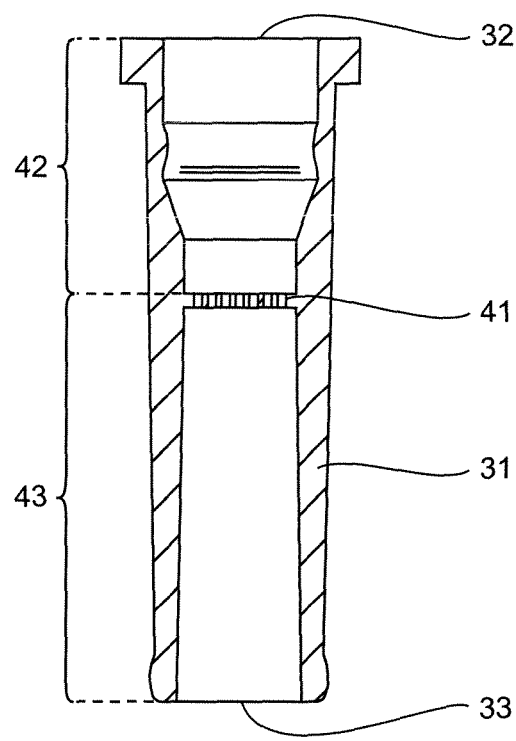
FIG. 4A shows an alternative of the storage means, including a separation wall.

The general principle of the invention is based on the use of means for storing an animal tissue sample, including at least two openings.

The invention thus proposes a tissue sampling device including sampling means having at least one cutting element intended to cut and collect an animal tissue sample, and new means for storing the sample. Once collected, the animal tissue sample stored in the storage means can be sent to a laboratory for analysis.

It is noted that the storage of tissue samples of an animal makes it possible in particular to subsequently identify the animal or detect diseases in said animal, in view of a microscopic examination or an extraction of a DNA sequence from the sample cells, for example.

Below, a specific embodiment of the invention is described, in which the storage means have a revolution shape defining a tube. Other shapes of the storage means can also be envisaged.

As shown in FIG. 3A, the storage means 31 according to the invention have at least two openings, a first opening 32 enabling a sample to be received, and a second opening 33 cooperating with removable closure means 34.

More specifically, as shown in FIG. 3B, the storage tube 31 according to this embodiment makes it possible to receive the cutting element 35 intended to cut and collect an animal tissue sample (or the punch to which it belongs), as well as the sample collected 36, by means of the first opening 32. Before the sample 36 is received, the first opening 32 can be closed by a lid. The lid is cut or torn by the cutting element 35 when the cutting element 35 and the sample 36 are inserted into the storage tube 31.

The cutting element 35 (or the punch to which it belongs) is considered to have a diameter slightly smaller than that of the storage tube 31. In this way, the cutting element 35 hermetically seals the first opening 32.

In particular, the sample 36 collected can fall into the storage tube 31, or remain wedged in a housing provided for this purpose in the cutting element 35. Such a housing opens toward the inside of the storage tube 31, but is closed toward the outside of said tube 31.

Thus, according to this embodiment, the sample 36 is collected by means of the cutting element 35 and assembled to the storage tube 31 during sampling, for example by blocking by wedging, without the user being required to directly handle the sample. The sample 36 in the storage tube 31 is not therefore polluted.

For the sampling, the cutting element 35 (or the punch) can be attached to a first jaw of a sampling tool such as a clamp, for example, and the storage means 31 can be attached to a second jaw of the tool. The closure means 34 can optionally be secured to the storage means 31 before sampling, in a closed state, or be secured to the storage means 31 only once the sampling has been performed. The sampling can be performed independently of, or in conjunction with the placement of the mark.

Once inserted into the storage tube 31, the sample can be stored for a more or less long period, on the order of several days to several years. Indeed, the first opening 32 is hermetically (or quasi-hermetically) sealed owing to the cutting element 35 or the punch including it, and the second opening 33 is hermetically or quasi-hermetically sealed owing to removable closure means 34, for example in the form of a cap (i.e., seal, lid, or plug).

It is noted to this end that the storage means 31 and the removable closure means 34 include complementary securing means, such as a threading or a grooving. The storage 31 and closure 34 means are, for example, reversibly secured by fitting, clipping, screwing and so on.

The storage means 31 and/or the closure means 34 can contain a preservative agent, such as an agent enabling the sample to be dried, called a drying agent. This agent can be in various forms, such as a powder, a gel, balls or pearls, and so on.

The removable closure means 34 according to the invention thus make it possible to remove the preservative agent before the sample 36 is treated. In this way, the preservative agent is prevented from reacting with a reagent used during the analysis of the sample 36. In addition, the removal of the drying agent before the treatment of the sample 36 makes it possible to reduce the amount of reagent or product necessary for treatment of the sample. Indeed, this product or reagent is no longer absorbed by the drying agent.

According to a specific embodiment of the invention, the storage means 31 include at least one wall defining two compartments each associated with one of the openings.

For example, as shown in FIG. 4A, the wall 41 defines a first compartment 42, associated with the first opening 32, and a second compartment 43, associated with the second opening 33. The wall 41 can be located in different places in the storage means 31. The only constraint to be respected is that it not hinder the insertion of the cutting element 35 and the sample 36, or the closure of the second opening 33. For example, if the storage means are in the form of a tube, the wall 41 has the form of a disk, solid or including one or more openings.

One of the roles of the wall 41 is to hold the sample 36 in the storage tube 31, in particular when the closure means 34 are detached from the storage tube 31 (open state). In this way, the sample 36 is secured in the first compartment 42, and is not accessible to a cheater.

In particular, this wall 41 is permeable, in the sense that it can allow liquids, gas, elements or particles to pass from one compartment to another. It is, for example, a membrane, a grid, a partition perforated by at least one opening, and so on.

In this way, it is possible to inject a reagent into the storage tube 31 by removing the closure cap 34, without having to remove or cut the cutting element 35 which blocks the first opening 32, or remove the sample 36.

In addition, the permeable wall makes it possible to remove a drying agent that is located in the first compartment 42 before the sample is treated. In this way, and as indicated above, any reaction of the reagent with the drying agent is prevented, and the amount of reagent used is limited since it is no longer absorbed by the drying agent.

The wall 41 also makes it possible to hold a drying agent which would be located in the second compartment 43 so that it does not come into direct contact with the sample 36 in the first compartment 42. The permeability of the wall however enables the drying agent to act on the sample 36 in order to at least partially absorb the water that it contains.

The drying agent, which is for example in the form of balls in the second compartment 43, can be removed by the closure cap 34 before analysis of the sample 36.

Figure 4B:
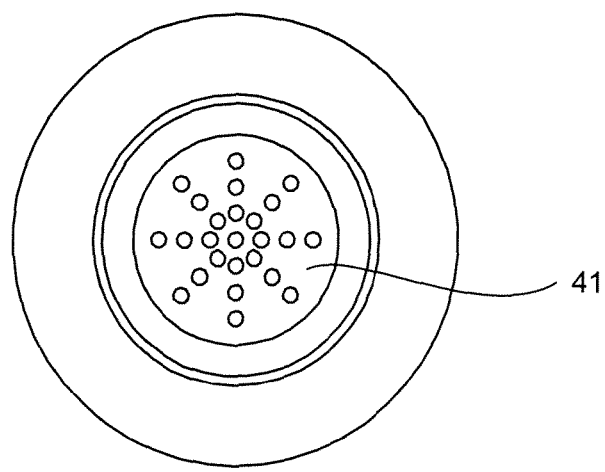
FIG. 4B shows an example of a wall.

The wall has, for example, the form of a grid or a partition perforated with at least one opening, as shown in FIG. 4B.

Other types of walls can be envisaged, such as a hard, flexible, elastic or fabric wall, perforated with one or more crosses, one or more holes, and so on. It simply must allow the passage of a reagent so that it can reach the sample.

According to an alternative, the closure means 34 can be made of a drying material, or the preservative agent can be integrated directly into the closure means 34. For example, the preservative agent is in the form of balls of drying product located between two partitions of the closure means, in which one of said partitions is not sealed and comes into contact with the inside of the storage means.

In this way, when the closure means 34 are in an open state, to have access to the inside of the storage means 31 and the sample 36, the preservative agent is not inside the storage means, and cannot "distort" the analysis of the sample.

According to an alternative embodiment, the closure means can be connected to storage means by means of a plastic part, a thread, and so on.

It is also noted that the storage means can have an identifier (for example, a number or a bar code). This identifier can also be placed on the closure means. However, because the closure means are removable, it is preferable to indicate this number directly on the storage means. In particular, when the sampling is implemented in conjunction with the placement of the mark, the storage means have an identifier identical to that appearing on the male and/or female portion of the mark.

Additional Aspects

Below, in reference to FIGS. 5 to 8, another aspect of the invention will be described, which enables an improvement of the separation of the sample and the cutting element and the use of liquid preservation means.

The patent application FR 08 58453, not published, proposes an animal tissue sampling device including:
sampling means having at least one cutting element intended to cut an animal tissue sample and
means for storing the sample.

According to this approach, the sampling means also include a push element capable of moving with respect to the cutting element, enabling the sample to be pushed into the storage means after the sample has been cut by the cutting element.

This novel approach to the collection of an animal tissue sample is particularly simple and fast for the user, and does not require the simultaneous placement of an identification mark. It indeed proposes using two distinct elements, mobile with respect to one another, including a cutting element enabling the tissue sample to be cut and a push element enabling the sample to be pushed into the storage means.

The use of distinct elements for these two operations has numerous advantages. For example, the cutting of tissues, then the pushing of the sample into the storage means make it possible to ensure a good cut of the sample, and to prevent the hair from remaining wedged between the walls and the cap of the storage means. These two distinct elements also make it possible to obtain a better sample. Indeed, as the cutting element is not intended to be inserted into the storage means, it is possible to increase the size of the cutting element, i.e. the length of the cutting edge, and therefore to increase the size of the sample collected.

According to a particular aspect, the push element can include a container containing at least one drying and/or preservative agent, in the form of a powder or granules. The use of such an agent enables the sample to dry.

During laboratory treatments, the tube is open (extraction of the tube head in which the push element is wedged), and a liquid solution is inserted, to obtain a reaction, according to the type of sampling desired (search for viruses, DNA sampling, etc.).

A disadvantage of this approach is that it is necessary to wait a more or less long time for the reaction to take place. In the laboratory, when a large number of tubes must be treated simultaneously, these waiting times are difficult to manage.

A pipette must then be inserted into the tube, in order to sample a portion of the liquid, for analysis thereof. It appears, in some cases, that the sample remains stuck to the pipette, and/or to other laboratory materials. This of course presents a problem when the systems are automated, for example in order to enable simultaneous sampling of 96 tubes, according to the SBS format. The presence of a sample extracted incorrectly from a tube can disrupt the treatments and "pollute" the other samples performed simultaneously.

Finally, it appears that the use of a solid drying agent is not functional enough to prepare the sample for a long preservation time, which is necessary in particular for DNA tests.

1. Anti-Return Means

The invention therefore proposes, according to a first aspect, providing the tube with sample anti-return means, such as a washer with flexible claws.

During sampling, the push element passes through this washer, as well as the sample. This extractor can in particular be part of a dual-movement clamp, in which the first actuates the punch in order to cut the ear, and the second actuates an extractor in order to push the cut sample into the tube, and thus extract it from the punch.

In the laboratory, when the tube is opened, as described in the aforementioned patent FR 08 58453 (the tube head in which the extractor is wedged is extracted), the sample remains inside the tube, owing to the claws of the washer. Thus, this washer enables more secure laboratory operations. In particular, the sample cannot remain secured to the pipettes or to other laboratory materials, and does not therefore disrupt the rest of the treatments.

2. Sealing Means

According to a second aspect of the invention, a lid is provided inside the tube, enabling a liquid to be preserved inside same. It can in particular be a liquid preservative agent and/or a liquid enabling a desired reaction for a laboratory treatment. This lid, for example, made of aluminum, is perforated for the passage of the sample and the extractor.

The insertion of the sample into this liquid solution can enable, according to the cases, preservation over a long period (for DNA follow-up) and/or a simplified laboratory treatment, since:
it is not necessary, after opening the tube, to insert a liquid in order to obtain the reaction;
it is also not necessary to wait for said reaction to take place.

3. Implementation of the Two Means

These two aspects, the anti-return means, for example in the form of a flexible washer, and the sealing means, can of course be implemented independently of one another. They can also be implemented simultaneously, in the same tube.

In this case, according to an alternative, it is possible for the same element to perform two functions, for example in the form of a pre-cut lid or a lid having weakened areas and stronger areas, designed so that, after the lid has been passed through by the sample and the extractor, it can perform the sample anti-return function.

4. Example Embodiment

The technique described above can be implemented in a device as shown by FIGS. 3A to 4B. It is also possible to implement it independently, as shown in FIGS. 5 to 8.

Figure 5:
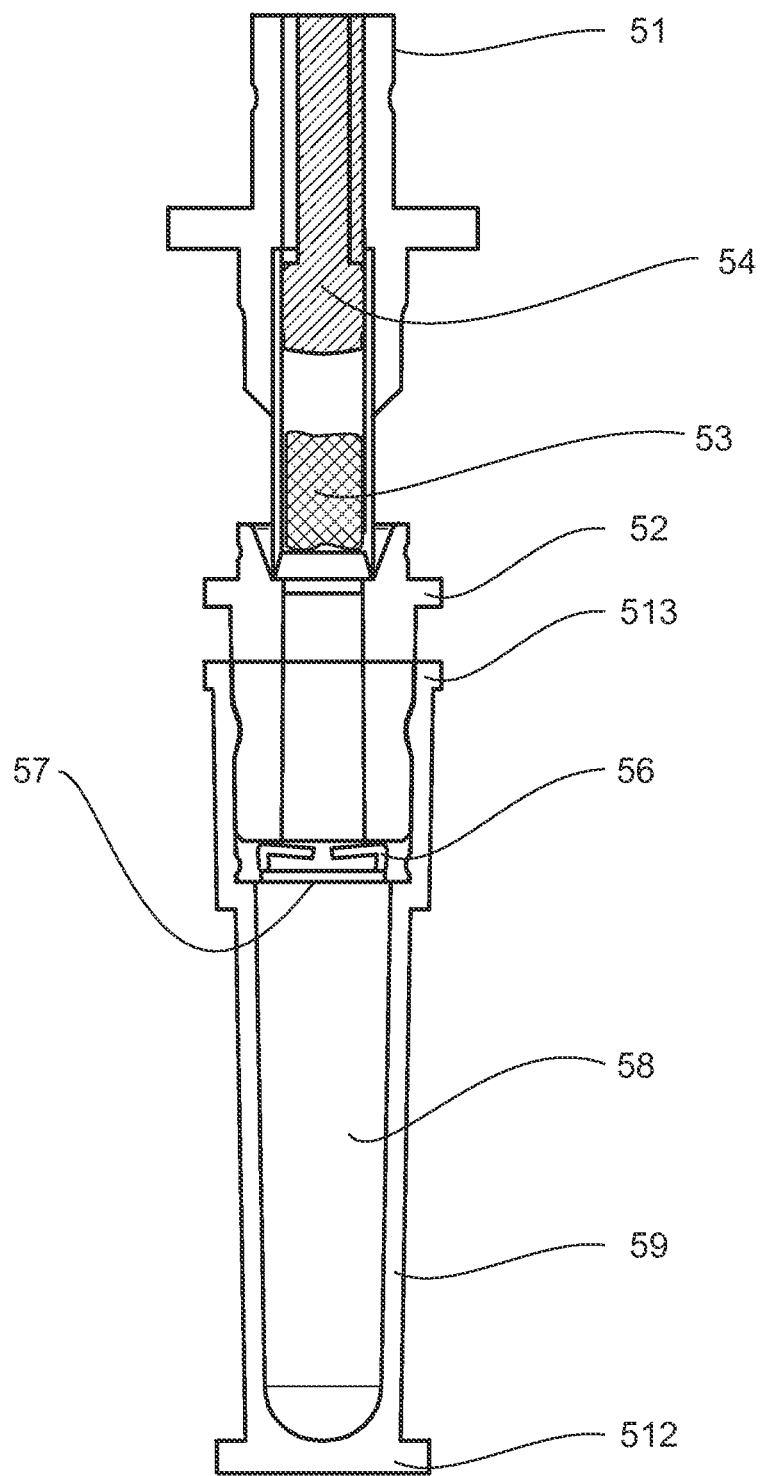
FIG. 5 shows another example of storage means, in which a sample is being inserted.

As shown in FIG. 5, the end of the clamp, and more specifically the punch support 51, is brought into contact with the end of the tube head 52, configured to receive it. The ear sample 53 cut is then located in the punch.

Figure 6:
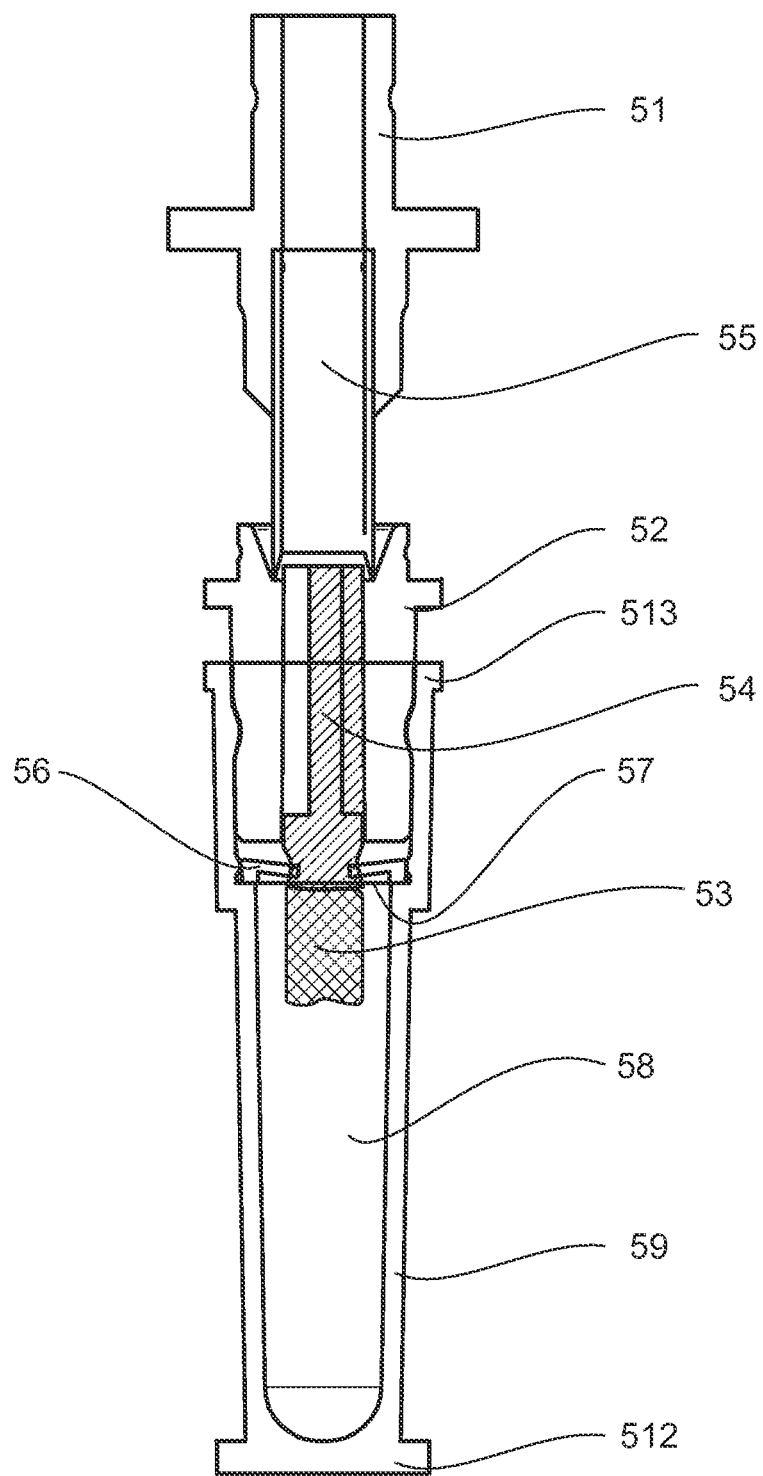
FIG. 6 shows the storage means of FIG. 5, in which the sample is placed in a liquid preservative.

As shown in FIG. 6, the extractor 54 slides into the cannula 55 and pushes the ear sample 53 into the tube, through the anti-return washer 56 and/or the sealing lid 57.

If a sealing lid 57 is present, a preservative liquid 58 and/or reagent is placed in advance (during production of the tube) in the tube 59 so that the sample is soaked in this liquid upon its insertion.

Figure 7:
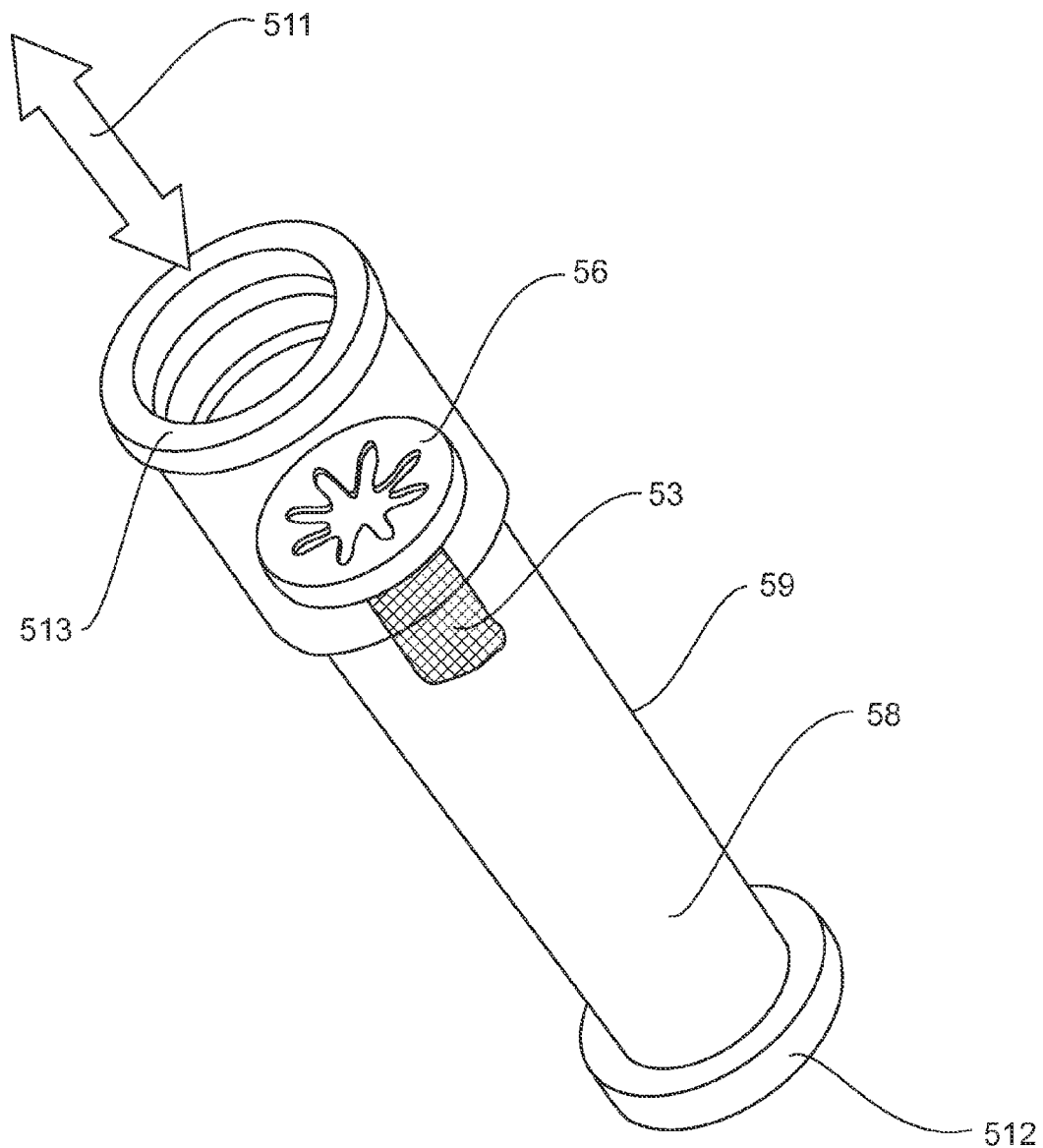
FIG. 7 is another view of the storage means of FIGS. 5 and 6.

As shown in FIG. 7, the punch support 51 is then removed, and the extractor 54 remains present in the tube head 510, to close the tube (therefore forming a cap). The end of said extractor 54 passes through the anti-return washer 56 so as to ensure that the sample 53 is integrally housed inside the tube 59.

Figure 8:
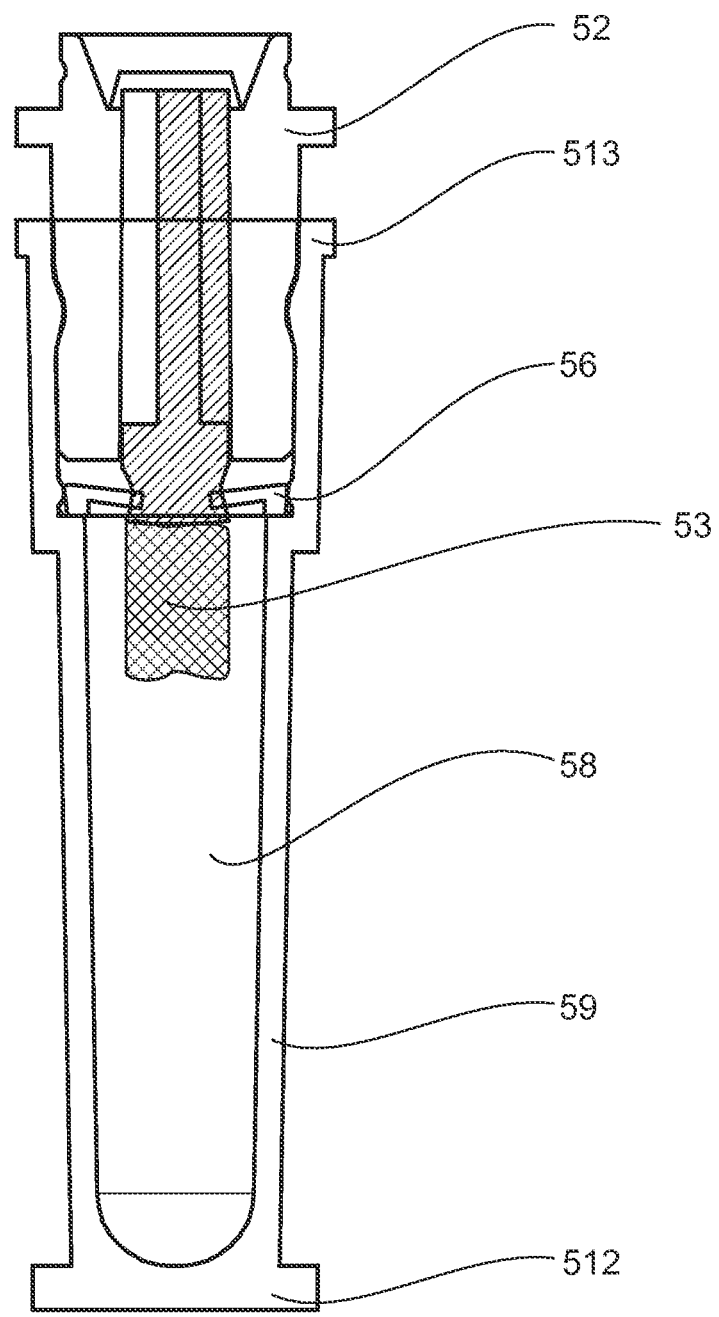
FIG. 8 is a cross-section view of the storage means of FIGS. 5 to 7.

In FIG. 8, the tube head 52 is removed in the laboratory to enable the various laboratory operations and in particular pipetting (511).

This FIG. 8 shows a specific form of the anti-return washer 56, having a central star-shaped cut, clearing a central access zone, sufficient for pipetting. The tabs of said washer are configured so as to prevent the sample 53 from falling out, even when it is attached, for example by suction, to a pipette.

The material used is therefore flexible enough to enable the sample to be inserted, and to prevent it from falling out. It is of course possible to provide specific shapes or degrees of movement in order to facilitate its insertion while preventing it from falling out.

In addition, the presence of the preservation liquid 58 at the start enables the sample 53 to be preserved for a long enough time, including for DNA analyses several years later, without it being necessary to extract the sample in order to place it in another container for preservation.

The preservative liquid 58 can also include one or more reagents, so that the laboratory treatment is simplified and accelerated: it is then simply necessary, indeed, to open the tube and collect the sample (without it being necessary, after opening, to introduce a liquid reagent, then wait for the reaction to take place before collecting the sample).

The external shape of the tube, and in particular its base 512 and/or its neck 513, are advantageously chosen so as to enable batch treatments, for example, adapted to the SBS format.

Of course, as explained above, this base 512 can be removable, or equipped with a removable cap, enabling pipetting, with the neck 513 remaining blocked by the push element, after sampling.

The invention claimed is:

1. An animal tissue sampling device comprising:
    a sampling means having at least one cutting element for collecting an animal tissue sample from an animal, and
    a storage means having a first end and a second end and defining an internal volume for storing a sample of animal tissue, wherein the at least one cutting element of the sampling means is dimensioned to be inserted in the storage means, the storage means having at least two openings:
        a first opening located at the first end of the storage means and dimensioned to enable said cutting element of the sampling means and said sample, to be received in the storage means, and wherein said cutting element seals said first opening after the insertion of the cutting element in the first opening; and
        a second opening located at the second end of the storage means, distinct from said first opening, and having a removable closure means that enables access to the internal volume of the storage means.

2. The device according to claim 1, wherein said storage means includes at least one wall defining two compartments within the storage means, a first compartment being defined between the first opening and the wall and a second compartment being defined between the wall and the second opening.

3. The device according to claim 2, wherein said at least one wall is permeable.

4. The device according to claim 2, wherein said at least one wall includes an element belonging to the group consisting of:
    a membrane,
    a grid, and
    a partition perforated with at least one opening.

5. The device according to claim 1, wherein the storage means contains at least one drying agent within the storage means' internal volume.

6. The device according to claim 1, wherein the closure means contains at least one drying agent.

7. The device according to claim 1, wherein the storage means has a cylindrical shape.

8. The device according to claim 1, wherein the closure means are reversibly securable to said storage means.

9. The device according to claim 1, wherein the closure means includes a hermetic seal reversibly secured to the storage means by a securing means selected from a group consisting of fitting, clipping, and screwing;
    said storage means comprising first securing means; and
    said closure means comprising second securing means complementary to said first securing means.

10. The device according to claim 1, wherein the sampling means further comprises an anti-return means dimensioned such that the sample may pass through the anti-return means, and disposed such that the sample is separated from the sampling means after the sample passed through the anti-return means.

11. The device according to claim 1, wherein said anti-return means are formed by a washer perforated at the washer's center, and having a plurality of flexible strips extending radially inward toward said center.

12. The device according to claim 1, wherein said storage means contains at least one of either a preservative or reactive liquid.

13. The device according to claim 12, wherein said storage means includes a sealing lid, isolating said liquid and configured to be perforated when a sample is inserted into said storage means.

14. Means for storing an animal tissue sample comprising:
    a storage means having a first end and a second end and defining an internal volume into which a cutting element for collecting an animal tissue sample is inserted after collection of said sample, the storage means having at least two openings:
        a first opening located at the first end of the storage means and dimensioned to enable said cutting element of the sampling means and said sample, to be received in the storage means, and wherein said cutting element seals said first opening after the insertion of the cutting element in the first opening; and
        a second opening located at the second end of the storage means, distinct from said first opening, and having a removable closure means that enables access to the internal volume of the storage means.

15. The device according to claim 1, wherein the sampling means further comprises a push element, wherein the push element is disposed in moving relation to the cutting element such that the movement of the push element urges the sample from the cutting element and into the storage means, and wherein the first opening of the storage means is dimensioned to receive at least a portion of the push element, and whereby the push element seals the sample means once received thereby.

16. The means according to claim 14, further comprising a push element disposed in moving relation to the cutting element such that the movement of the push element urges the sample from the cutting element and into the storage means, and wherein the first opening of the storage means is dimensioned to receive at least a portion of the push element, and whereby the push element seals the sample means once received thereby.

17. An animal tissue sampling device comprising:
a sampling means having at least one cutting element for cutting an animal tissue sample from an animal,
a push element disposed in moving relation to the sampling means; and
a storage means having a first end and a second end and defining an internal volume for storing a sample of animal tissue, wherein the push element of the sampling means is dimensioned to be inserted in the storage means, the storage means having at least two openings:
  a first opening located at the first end of the storage means and dimensioned to enable said push element of the sampling means and said sample, to be received in the storage means, and wherein said push element seals said first opening after the insertion of the push element in the first opening, and
  a second opening located at the second end of the storage means, distinct from said first opening and having a removable closure means that enables access to the internal volume of the storage means; and
wherein the movement of the push element relative to the cutting element urges the sample from the cutting element and into the storage means.

18. An animal tissue sampling device comprising:
a sampling means having at least one cutting element for collecting an animal tissue sample from an animal, and
a storage tube defining an internal volume for storing a sample of animal tissue, wherein the at least one cutting element of the sampling means is dimensioned to be inserted in the storage tube, the storage tube having at least a first opening located at a first end and a second opening located at a second end:
  said first opening dimensioned to enable said cutting element of the sampling means and said sample, to be received in the storage tube, and wherein said cutting element seals said first opening after the insertion of the cutting element in the first opening; and
  said second opening distinct from said first opening and having a removable closure means that enables access to the inside of the storage tube.

* * * * *